United States Patent [19]
Carver et al.

[11] Patent Number: 5,202,448
[45] Date of Patent: Apr. 13, 1993

[54] PROCESSES OF CONVERTING TAXANES INTO BACCATIN III

[75] Inventors: David R. Carver; Timothy R. Prout, both of Boulder; Hernita A. Ewald, Englewood; Donia L. Henderson, Boulder, all of Colo.

[73] Assignee: NaPro BioTherapeutics, Inc., Boulder, Colo.

[21] Appl. No.: 930,840

[22] Filed: Aug. 14, 1992

[51] Int. Cl.$^5$ ............................................. C07D 305/14
[52] U.S. Cl. .................................................... 549/510
[58] Field of Search ........................................ 549/510

[56] References Cited
PUBLICATIONS

Miller et al.; JOC, 46, 1469 (1981).
Magri et al., JOC, 51, 3239 (1986).

Primary Examiner—Marianne M. Cintins
Assistant Examiner—Michael B. Hydorn
Attorney, Agent, or Firm—Timothy J. Martin; Dana S. Rewoldt

[57] ABSTRACT

The present invention relates to a process of converting partially purified taxane mixtures into Baccatin III. The process for the preparation of Baccatin III includes contacting a mixture containing at least one taxane compound having an ester linkage at the C-13 position with at least one borohydride reducing salt in a reaction solvent in the present of a Lewis acid.

21 Claims, No Drawings

PROCESSES OF CONVERTING TAXANES INTO BACCATIN III

FIELD OF THE INVENTION

The present invention relates to a process of converting partially purified taxane mixtures into Baccatin III. Specifically, the present invention relates to a process using borohydride reducing salts in the presence of Lewis acids to convert taxol, cephalomannine and other taxanes into related baccatins.

BACKGROUND OF THE INVENTION is a diterpernoid found in the Western Yew, (*Taxus brevifolia*), has shown anticancer activities in clinical trials. Extensive testing of taxol has been difficult due to its short supply. Attempts at total synthesis of taxol has so far been unsuccessful. However, significant strides have been made in the semi-synthesis of taxol from other naturally occurring taxanes such as Baccatin III and 10-deacetylbaccatin III. At least three different methods of converting Baccatin III and 10-deacetylbaccatin III into taxol have been reported.

One can observe that the structure of Baccatin III (2) has the basic diterpenoid structure of taxol without the side chain at the C-13 position. Thus, Baccatin III and the other related Baccatins are important starting materials in taxol semi-synthesis. The significance of Baccatin III may increase as more taxol cancer testing is performed. Already it appears that water soluble taxol-like compounds with slightly modified C-13 side chains may be more desirable as cancer drugs than the natural occurring less soluble taxol. This increases the unresolved need for Baccatin III as a starting material to synthesize taxol and second and third generation taxol-like compounds.

The present source of Baccatin III is extraction from the English Yew (*Taxus Baccatta*). The supply of this raw material is limited. Conversion of taxol and cephalomannine into Baccatin III is a viable method of increasing the supply of Baccatin III.

Miller reported that cephalomannine was converted in a 19% yield to Baccatin III by methanolysis in the presence of sodium bicarbonate. See, *Journal of Organic Chemistry*, Volume 46, pp. 1469–1474 (1984). Preparation of a 97% yield of Baccatin III from pure taxol was reported by Magris, et al. See, "Modified taxols, 3. Preparation and Acylation of Baccatin III", *Journal of Organic Chemistry*, Vol. 51, pp. 3239–3242, 1986. The preparation of Baccatin III according to the Magris, et al process was performed as follows: a 100 mg sample of pure taxol in dry $CH_2CL_2$ (2.0 mL) was allowed to react with $Bu_4NBH_4$ (50 mg) for one hour, and the reaction was quenched with 0.5 mL of AcOH. The mixture was stirred ten minutes, evaporated, and the product isolated by preparative TLC. This process was reported to give a 97% yield of Baccatin III from pure taxol.

The Magris, et al paper also indicated that this reaction was run on a starting material consisting of an unpurified taxol/cephalomannine mixture and the result was a reduced yield of Baccatin III compared to using pure taxol as the starting material. High yield conversion of pure taxol to Baccatin III is extremely useful in the laboratory where pure taxol is available. However, there is a need for a high yield process to convert crude taxane mixtures (containing taxol/cephalomannine and other taxanes) into Baccatin III.

In the commercial extraction of taxol from yew tree material, significant quantities of taxanes including taxol and cephalomannine are generated These mixtures contain useful taxanes (which are thrown away as by-products in the purification of taxol). The Magris, et al process has not demonstrated particularly high yield results when partially purified mixtures containing low percentages of taxol and cephalomannine are converted into Baccatin III.

In large scale processing of taxol for commercial use, the cost associated with achieving the Magris, et al yield is not economically feasible. The Magris, et al process uses tetrabutylammonium borohydride, an expensive reducing salt. Furthermore, this procedure is run at 0° C. which adds refrigeration costs to the final product. Most taxane extraction processes result in by-products containing some taxol, cephalomannine and significant amounts of other substances. Therefore, there remains a need for a high yield inexpensive process of converting these partially purified mixtures of taxanes including taxol and/or cephalomannine into Baccatin III.

SUMMARY OF THE INVENTION

An object of the present invention is to convert partially purified organic by-products of the taxane extraction process into Baccatin III.

Another object of the present invention is to provide a method of converting selected taxanes into Baccatin III.

A further object of the present invention is to provide a simple, high-yield method of preparing Baccatin III at room temperature.

Still a further object is to provide an inexpensive high yield method of converting a partially purified mixture of taxol/cephalomannine and other substances into Baccatin III.

This invention provides a process for the preparation of Baccatin III by contacting a mixture containing at least one taxane compound having an ester linkage at the C-13 position with at least one borohydride reducing salt in a reaction solvent in the presence of a Lewis acid. If the mixture contains 15%–50% taxol by weight, the preferred reaction solvent is tetrahydrofuran (an apolar, donor solvent). When the mixture contains 50% taxol by weight, the preferred reaction solvent is dichloromethane. If the mixture contains less than 15% taxol by weight, the reaction solvent is selected from a group of glyme, diglyme, triglyme or alternatively THF. The preferred Lewis acid is a metal halide such as tin(II) chloride or cobalt(II) chloride.

This invention further provides a process of preparing Baccatin III by contacting a mixture containing at least one taxane compound constituent having an ester linkage at the C-13 position with a borohydride reducing salt, using an aromatic hydrocarbon, preferably toluene as the solvent.

Furthermore, this invention provides a process of preparing Baccatin III, by contacting a mixture containing taxol and at least one other taxane compound having an ester linkage at the C-13 position with a borohydride reducing salt in a reaction solvent wherein the taxol in the mixture is not converted to Baccatin III.

DESCRIPTION OF THE PRESENT INVENTION

The present invention relates to high yield processes for converting partially purified mixtures of taxanes containing taxol and cephalomannine into Baccatin III. The Magris, et al paper reported that their process had been run on a partially purified taxane mixture containing taxol and cephalomannine, however, the Baccatin III yield from this mixture was only reported as "good". Therefore, as a baseline by which to compare the present invention, the Magris, et al process was run on a mixture of taxanes which contained a high level of taxol. In this experiment, the Magris, et al process was performed at 0° C. on 51 mg of a dry partially purified taxane mixture containing 47% taxol and 1.0% cephalomannine (as determined by HPLC) The procedure was run for one hour on this material in dichloromethane, with tetrabutylammonium borohydride as the reducing salt. The yield of Baccatin III from the mixture was 66.0%. This is a significant yield; although, the yield is substantially less than the 97% yield of Baccatin III from pure taxol. This 66% yield is therefore the baseline by which the following examples can be compared.

The preferred embodiment of the present invention includes contacting a mixture containing some taxanes 15 with a borohydride reducing salt in a reaction solvent in the presence of a Lewis acid in less than and up to stoichiometric quantities. In the preferred process sodium borohydride is employed due to the higher cost associated with the use of tetrabutylammonium borohydride. The preferred Lewis acids are compounds such as metal halides. The test to determine the viability of a Lewis acid is two-fold. One, the Lewis acid should covalently bond with strong nucleophiles and second, the Lewis acid should not react with the borohydride to form boranes. Magnesium chloride (which is not expected to covalently bond with strong nucleophiles) was tested and did not increase the yield of Baccatin III. More covalent Lewis acids such as $SnCl_2$ and $CoCl_2$ increase the Baccatin III yield significantly above the baseline yield of the Magris, et al procedure.

The types of borohydride reducing salt, reaction solvent and Lewis acid used in the alternative embodiments of the present invention have been selected to result in a commercially viable, high yield process of converting taxanes into Baccatin III.

The reaction solvents used in the embodiments of the present invention are selected based on the levels of taxol in the starting material. Glyme ($CH_3OCH_2CH_2OCH_3$) works slightly better in starting material with less than 15% taxol; although tetrahydrofuran (THF) is also useful in this range. THF as a reaction solvent is preferred in starting materials with 15% to 45%–50% taxol purity. In starting materials having 45%–100% taxol purity, dichloromethane as a reaction solvent yields Baccatin III in large amounts. In spite of solubility problems, toluene as a reaction solvent resulted in a substantially higher yield of Baccatin III than dichloromethane, in starting material having the same 45%–100% taxol purity.

The processes of the present invention yield a higher percentage of Baccatin III from a taxane mixture at room temperature than the baseline Magris, et al process yields at 0° C. The processes of the present invention employ different reaction solvents for different levels of taxol purity in the starting material and different Lewis acids to increase the yield of Baccatin III from a starting material formed of partially purified taxanes.

In the first embodiment of the present invention, a 76.7% yield of Baccatin III was prepared by mixing the starting material with the reaction solvent toluene and the reducing borohydride salt tetrabutylammonium borohydride. The starting material contained 47% taxol, 1.0% cephalomannine and other substances. Baccatin III was converted in a 76.7% yield at 0° C. after a reaction time of one week. This yield of Baccatin III was realized despite the anticipated and actual solubility problems associated with the use of toluene in this reaction.

In the second embodiment of the present invention, Baccatin III was prepared by contacting sodium borohydride in dichloromethane with a starting material having 15.0% taxol and 3.2% cephalomannine at 0° C. After sixteen hours of reaction, Baccatin III was produced in an 85.8% yield by HPLC analysis. The advantage of using sodium borohydride over using tetrabutylammonium borohydride is primarily the expense. The former being about $0.11 a gram, while the later is $1.00 a gram. Although the Magris, et al reference describes use of sodium borohydride to convert a pure taxol to Baccatin III, this borohydride reducing salt was used with propanol and resulted in the undesired epimerization at the C-7 position. Magris, et al abandoned the sodium borohydride and used the more expensive tetrabutylammonium borohydride in association with dichloromethane to get the 97% yield of Baccatin III from pure taxol.

As noted in the Magris, et al paper, the borohydride used in forming Baccatin III are believed to be reducing esters by delivery of a hydride ion to the ester carbonyl group. What was not resolved by this reference was the decrease in the ability to cleave the ester that resulted if the reactive borohydride reducing salt (especially if tetrabutylammonium borohydride is employed) was in contact with protic compounds. Of course, a variety of protic compounds such as water and alcohols are found in partially purified taxane starting material—some protic substances are naturally occurring in the plant material (Taxus) and some are added in the various extraction and purification steps. Additionally, hydroxide and alkoxide basic ions may be present. These materials cause undesired epimerization and cleavage and can result in substantially decreased yields of Baccatin III.

To counteract these undesirable compounds in the starting material, the reaction of the preferred embodiment of the present invention adds Lewis acids in less than and up to stoichiometric quantities. The metal halides $SnCl_2$ and $CoCl_2$ have proven especially useful Lewis acids in this process. These metal halides in the presence of oxygen anions rapidly react to make metal oxides with the subsequent release of nontaxane reacting $Cl^-$ anions. Thus, many undesirable components of the starting material are effectively neutralized, allowing the borohydride to react more specifically with taxanes in the mixture.

In the third embodiment, the addition of 10% tin chloride (based on the taxol in the starting material) to tetrabutylammonium borohydride in dichloromethane at 0° C. for one hour resulted in a 121.7% yield of Baccatin III. It would appear material other then just the cephalomannine and taxol in the starting material was cleaved to produce Baccatin III. It is hypothesized that certain taxol compounds may be bound to sugars and other biological material and that these may have been converted to Baccatin III in this process.

In the fourth preferred embodiment of the present invention, a 72% yield of Baccatin III was prepared by contacting a taxane mixture starting material containing 3.5% taxol and 2.3% cephalomannine, using the reaction solvent glyme, with sodium borohydride/cobalt chloride pellets, which contain 7% cobalt chloride pellets. The reaction was run at room temperature for one hundred and forty-four hours.

In the fifth alternative preferred embodiment of the present invention, a similar reaction, using starting material with the same taxane percentage, in glyme with sodium borohydride in the presence of tin chloride (0.1%) resulted in a 66% Baccatin III yield after seventy-two hours at room temperature.

In a sixth alternative embodiment of the present invention, a 71% Baccatin III yield resulted from the same starting material in THF with sodium borohydride in the presence of (0.1%) tin chloride (based on content of taxol in the starting material).

The seventh embodiment resulted from the process of testing various reaction solvents with the sodium borohydride reducing salt. A surprising result was achieved when ethanol was used, and the reaction was run at $-30°$ C. The borohydride reducing salt selectively cleaved cephalomannine and some other taxanes but not taxol. The Baccatin III yield from this reaction was 58%, and 100% of the taxol remained after twenty-four hours. The reaction's ability to selectively cleave the starting material to Baccatin III in the presence of a mixture of taxanes has significant utility in taxane purification and extraction processes.

The following non-limited examples provide specific processes for preparing Baccatin III from a partially purified taxane mixture or purified taxane samples. All scientific and technical terms have the meanings as understood by one with ordinarily skill in the art. HPLC in the following examples was carried out on an apparatus consisting of a Spectra Physics 8800 Ternary Pump, a Rheodyne hand injector Spectra Physics SP8780 (auto-sampler), an SP4400 Chromjet integrator and a Spectra-100 (variable wavelength detector). $^1H$-NMR spectra were obtained using a Varian VXR 300S $MH_z$ spectrometer. Elemental analysis was performed by Juffman Laboratories (Golden, Colo.). Various methods of purifying the Baccatin III produced by the present invention are known and understood by those skilled in the art and the purification method presented in Example I is solely listed by way of example and is not intended to limit the invention.

EXAMPLE I (Prior Art)

Table Ia

The reaction conditions in example I are as follows:

| Reaction solvent | $CH_2Cl_2$ |
|---|---|
| Reaction temperature (degrees C.) | 0 |
| Reaction time | 1 hour |
| Reducing salt | tetrabutylammonium borohydride |
| Additional reagents | none |

51 mg of taxanes (starting material) having 47.04% taxol and 1.04% cephalomannine was stirred into 2.0 mL dichloromethane in a 25 mL round bottom flask under a nitrogen gas atmosphere. After cooling the solution to 0° C. in an ice bath, 25 mg of tetrabutylammonium borohydride was added. The mixture was allowed to stir for one hour and the reaction was quenched by addition of 0.5 mL of AcOH.

The organic solution containing Baccatin III was poured into 25 mL/g of 50% by volume acetic acid/$H_2O$. The organic solution was repeatedly extracted with an immiscible organic solvent. In this instance dichloromethane was used. The organic phase was collected and dried over anhydrous sodium sulfate. The organic phase was removed in vacuo to form a viscous oil. The residue was purified by flash chromatography on silica gel using nitrogen pressure eluting with dichloromethane/5% methanol. The selected fractions were evaporated to dryness under reduced pressure (20 mm Hg).

The dry organic material was recrystallized from a 15% solution of methanol/$H_2O$(80/20) to produce 11.13 mg of Baccatin III in a 66.03% yield.

TABLE Ib

| Starting material (mg) | 51.000 |
|---|---|
| % taxol | 47.040 |
| Taxol weight (mg) | 23.990 |
| % Cephalomannine | 1.040 |
| Cephalomannine weight (mg) | 0.530 |
| Theoretical yield Baccatin III (from taxol in mg) | 16.481 |
| Theoretical yield Baccatin III (from Ceph in mg) | 0.374 |
| Total theoretical yield (mg) | 16.855 |
| Actual yield Baccatin III (mg) | 11.130 |
| % yield Baccatin III (with respect to taxol) | 67.532 |
| % yield Baccatin III (with respect to taxol and Ceph) | 66.033 |
| Taxol remaining (mg) | 11.710 |
| % taxol used | 51.189 |
| Cephalomannine remaining (mg) | 0.000 |
| % cephalomannine used | 100.00 |

The resulting Baccatin III had the following characteristics, the melting point and elemental analysis for $C_{31}H_{38}O_{11}$ (done by Huffman Laboratories, Golden, Colo.) for the product matched those reported previously for Baccatin III.

The proton nuclear magnetic resonance spectrum (300 Mhz; deuterated chloroform; chemical shift in ppm; coupling constants J in Hz): 1.11 (s.6H), 2.06

(s,3H), 2.25 (s,3H), 2.29 (s,3H), 2.31 (m,3H), 2.57 (m,1H), 3.88 (d, J=6.8, 1H), 4.15 (d, J=8.3, 1H), 4.31 (d, J=8.3, 1H), 4.47 (m, 1H), 4.90 (t, J=8.1, 1H), 4.98 (dd; J=8.7, 1.2; 1H), 5.62 (d, J=7.1, 1H), 6.32 (s, 1H), 7.49 (t, J=7.3, 2H), 7.61 (td; J=7.7, 1.2; 1H), 8.11 (d, J=7.7, 2H).

EXAMPLE II

The reaction conditions in Example II are as follows:

TABLE IIa

| Reaction solvent | Toluene |
|---|---|
| Reaction temperature (degrees C.) | 0 |
| Reaction time | 1 week |
| Reducing salt | tetrabutylammonium borohydride |
| Additional reagents | none |

The starting material was formed of partially purified taxanes collected during the process of extracting and purifying taxol from *Taxus brevifolia* plant biomass. The starting material was determined to contain 47.04% taxol and 1.04% cephalomannine by HPLC. A 55 mg quantity of the starting material was combined with 2.0 mL of toluene in a 250 mL round bottom flask equipped with a magnetic stirrer, under a nitrogen gas atmosphere. After the dissolution was complete, the solution was cooled to 0°0 C. Tetrabutylammonium borohydride (40 mg) was added and the heterogeneous mixture was allowed to stir. The reaction was monitored by TLC, and due to the slowness of the reaction, this reaction was allowed to proceed for a week. The following prior art purification procedure was employed. The reaction was poured into 1 mL of 50% acetic acid/H₂O and allowed to stir until the evolution of gas ceased. The mixture was then diluted with 10 mL of water and 10 mL of an immiscible organic solvent. The organic layer was extracted three times, collected, reduced in vacuo and purified by flash chromotography eluting with dichloromethane/5% methanol. Fractions containing Baccatin III were evaporated to dryness and recrystallized from methanol/H₂O (80:20). The yield of 13.95 mg represented a 76.7% Baccatin III yield. Proton NMR and the melting point of the Baccatin III matched values as previously reported in the literature.

TABLE IIb

| | |
|---|---|
| Starting material (mg) | 51.000 |
| % taxol | 47.040 |
| Taxol weight (mg) | 25.872 |
| % Cephalomannine | 1.040 |
| Cephalomannine weight (mg) | 0.572 |
| Theoretical yield Baccatin III (from taxol in mg) | 17.774 |
| Theoretical yield Baccatin III (from Ceph in mg) | 0.403 |
| Total theoretical yield (mg) | 18.177 |
| Actual yield Baccatin III (mg) | 13.950 |
| % yield Baccatin III (with respect to taxol) | 78.487 |
| % yield Baccatin III (with respect to taxol and Ceph) | 76.745 |
| Taxol remaining (mg) | 2.370 |
| % taxol used | 90.840 |
| Cephalomannine remaining (mg) | 0.249 |
| % cephalomannine used | 56.469 |

Toluene has a dielectric constant of approximately 2.3 making it an apolar solvent. Partially purified mixtures of taxanes obtained in taxol extraction processes often contain polar material due to the addition of H₂O and alcohol during the extraction process. Therefore, the person with ordinary skill in the art would hesitate to select toluene due to the potential solubility problems associated with dissolving the partially polar starting material in toluene. Therefore, it was highly surprising to realize that in spite of the solubility problems associated with toluene, the use of toluene as the solvent, resulted in a 76.7% yield of Baccatin III when the reaction was allowed to continue to completion. The result indicates a 10% higher yield than the baseline procedure. Similarly, other aromatic hydrocarbons such as benzene, 1, 3, 5 methylbenzene, 1, 2-dimethylbenzene, 1, 3-dimethylbenzene, 1, 4-dimethylbenzene have potential solubility problems but could be substituted for toluene in this procedure.

EXAMPLE III

The reaction conditions in Example III are as follows:

TABLE IIIa

| Reaction solvent | CH₂Cl₂ |
|---|---|
| Reaction temperature (degrees C.) | 0 |
| Reaction time | 16 hours |
| Reducing salt | NaBH₄ |
| Additional reagents | none |

The use of tetrabutylammonium borohydride in a taxane reaction on a commercial basis is highly undesirable due to the expense of the borohydride. An inexpensive substitute for tetrabutylammonium borohydride is sodium borohydride. In the past sodium borohydride has been avoided in taxane reactions because when used with isopropyl alcohol in a reaction to convert taxol to Baccatin III, undesirable products such as the diol 8 and undesirable reactions such as epimerization of the C-7 hydroxyl group to give Baccatin V have resulted. In order to avoid these problems, the sodium borohydride and isopropyl alcohol solvent have been substituted with tetrabutylammonium borohydride in dichloromethane.

A solution formed of 50.2 mg of the dry mixture of taxane (starting material) with 2.0 mL of dichloromethane was cooled to 0° C. The solution was then combined with 4.7 mg of sodium borohydride. The reaction was stirred at 0° C. for sixteen hours. The Baccatin III in the reaction was then purified and collected by the prior art procedure as indicated in Examples I and II. The proton NMR and melting point of the product matched values of Baccatin III previously reported in the literature.

TABLE IIIb

| | |
|---|---|
| Starting material (mg) | 50.200 |
| % taxol | 15.100 |
| Taxol weight (mg) | 7.701 |
| % Cephalomannine | 3.180 |
| Cephalomannine weight (mg) | 1.622 |
| Theoretical yield Baccatin III (from taxol in mg) | 5.290 |
| Theoretical yield Baccatin III (from Ceph in mg) | 1.144 |
| Total theoretical yield (mg) | 6.434 |
| Actual yield Baccatin III (mg) | 5.520 |
| % yield Baccatin III (with respect to taxol) | 104.338 |
| % yield Baccatin III (with respect to taxol and Ceph) | 85.792 |
| Taxol remaining (mg) | 3.560 |
| % taxol used | 53.772 |

TABLE IIIb-continued

| | |
|---|---|
| Cephalomannine remaining (mg) | 0.952 |
| % cephalomannine used | 41.300 |

The Magris, et al procedure shown in Example I was run on a highly purified starting material (47% taxol) and only yielded 66% Baccatin III. In contrast, the starting material in Example III contained only 15% taxol and yet the yield of Baccatin III was 85%. Furthermore, substantial production of undesirable product was not encountered.

EXAMPLE IV

The reaction conditions in Example IV are as follows:

TABLE IVa

| | |
|---|---|
| Reaction solvent | CH$_2$Cl$_2$ |
| Reaction temperature (degrees C.) | 0 |
| Reaction time | 1 hour |
| Reducing salt | tetrabutylammonium borohydride |
| Additional reagents | SnCl$_2$ (10%) |

A 50 mg quantity of starting material (having 47% taxol) was combined with 2.0 mL of dichloromethane under a nitrogen gas atmosphere in a 25 mL flask equipped with a magnetic stirrer. After dissolution was complete reaction was cooled to 0° C. in an ice bath. Then 2.5 mg of tin chloride (a 10% molar percentage based on taxol content of the starting material) and 25 mg of tetrabutylammonium borohydride were added to the reaction. The reaction was permitted to stir for one hour and then was poured into 10-25 ml/g of a 50% by volume acetic acid/water solution to quench the reaction. The mixture was repeatedly extracted with an immiscible organic solvent. The solvent used in this example was dichloromethane. The organic phase was collected and reduced in vacuo. This material was purified by flash chromotography eluting with a dichloromethane/5% methanol mixture. The fractions were collected and reduced in vacuo and recrystallized from methanol/water. The result was a 121.0% yield of Baccatin III. Proton NMR and melting point data collected matched those for Baccatin III.

TABLE IVb

| | |
|---|---|
| Starting material (mg) | 50.000 |
| % taxol | 47.040 |
| Taxol weight (mg) | 23.520 |
| % Cephalomannine | 1.040 |
| Cephalomannine weight (mg) | 0.520 |
| Theoretical yield Baccatin III (from taxol in mg) | 16.158 |
| Theoretical yield Baccatin III (from Ceph in mg) | 0.367 |
| Total theoretical yield (mg) | 16.525 |
| Actual yield Baccatin III (mg) | 20.110 |
| % yield Baccatin III (with respect to taxol) | 124.459 |
| % yield Baccatin III (with respect to taxol and Ceph) | 121.697 |
| Taxol remaining (mg) | 7.450 |
| % taxol used | 68.325 |
| Cephalomannine remaining (mg) | 0.000 |
| % cephalomannine used | 100.000 |

A variety of taxanes having the diterpenoid structure have been reported in the literature. It is anticipated that taxanes having different C-13 side chains than the C-13 side chain of cephalomannine or taxol would be present in a mixture obtained from a taxol extraction process. One group of taxane having different C-13 side chains are "bound taxanes". These taxanes appear to be attached or "bound" to other biological molecules such as sugars; at least one known "bound taxane" is 7-xylosyltaxol. The 121% yield results from the cleavage of taxanes which did not appear as taxol or cephalomannine in the HPLC analysis of the starting material. The ability to cleave these unidentified taxanes results in a very desirable increase in the Baccatin III yield.

EXAMPLE V

The reaction conditions in Example V are as follows:

TABLE Va

| | |
|---|---|
| Starting material (sm) | 10 g |
| Taxol in starting material | 350 mg |
| % taxol in starting material | 3.5% |
| Ceph in starting material | 230 mg |
| % Ceph in starting material | 2.3% |
| Reducing salt | NaBH$_4$ 10:1 |
| Additional reagents | SnCl$_2$ (.1%) |

10 g of taxane (starting material) containing a taxol (3.5%) a cephalomannine (2.3%) was stirred into 200 mL of THF in a 500 mL round bottom flask under a nitrogen gas atmosphere. Sodium borohydride in a 10:1 stoichiometric ratio based on the starting material and 0.1% tin chloride (based on molar % of taxol in the starting material) were added to the mixture. The reaction was allowed to run at room temperature for seventy-two hours. After this period, the organic solution containing the Baccatin III was purified by the following method. The organic solution was poured into 10 mL per gram of 50% by volume acetic acid/H$_2$O. The organic solution was then repeatedly extracted with an immiscible organic solvent, in this case THF. The organic phase was collected, dried over anhydrous sodium sulfate, and evaporated in vacuo to a viscous oil. This oil was purified by flash chromatography eluting with dichloromethane/5% methanol. The selected fractions were then reduced to dryness under reduced pressure (20 mm mercury). The dry organic material was then recrystallized from a 15% solution of methanol/water (80:20). 171 mg of Baccatin III were recovered resulting in a 71% yield. The $^1$H NMR analysis and melting point of the product matched those previously reported for Baccatin III.

TABLE Vb

| | |
|---|---|
| Reaction Solvent | THF |
| with | NaBH$_4$ |
| Reaction temp C. | room temperature |
| Reaction time | 72 hours |
| Theoretical yield Baccatin III | 241 mg |
| Actual yield Baccatin III (hplc) | 171 mg |
| % yield Baccatin III | 71% |
| Taxol remaining (hplc) | 28 mg |
| % taxol remaining | 8% |
| Cephalomannine remaining | 42 mg |
| % cephalomannine remaining | 18% |

In contrast, the same procedure as described in Example V was run on 30 grams of starting material having the same taxol/cephalomannine percentages. The reaction solvent used was dichloromethane (as was used in the Magris, et al procedure). The Baccatin III yield was only 36%, 260 mg (a higher yield resulted from 10 g of material) as analyzed by TLC to determine the completion of the reaction. Based on TLC analysis, the reaction in dichloromethane was run for one hundred twenty hours versus seventy-two hours.

EXAMPLE VI

The reaction conditions and starting material in Example VI are as follows:

TABLE VIa

| | |
|---|---|
| Starting material | 10 g |
| Taxol in starting material | 350 mg |
| % taxol in starting material | 3.5% |
| Cephalomannine in starting material | 230 mg |
| % cephalomannine in starting material | 2.3% |
| Reducing salt | NaBH$_4$ 10:1 |
| Additional reagents | SnCl$_2$ (.1%) |

10 g of taxane starting material containing a taxol (3.5%) and cephalomannine (2.3%) was stirred into 200 mL of glyme in a round bottom flask under a nitrogen gas atmosphere. Sodium borohydride (10:1 stoichiometric ratio based on the starting material) and (0.1%) tin chloride (based on molar percentage of taxol in starting material) were added to the reaction. The reaction was allowed to run at room temperature for seventy-two hours. After this time, the organic solution containing the Baccatin III was purified by the following method. The organic solution was poured into 10-25 mL per gram of 50% by volume acetic acid/H$_2$O. The organic solution was then repeatedly extracted with an immiscible organic solvent, in this case glyme. The organic phase was collected, dried over an anhydrous sodium sulfate and evaporated in vacuo to a viscous oil. The oil was purified by flash chromotography eluting with dichloromethane/5% methanol. The selected fractions were then evaporated to dryness under reduced pressure (20 mm Hg). The dry organic material was then recrystallized in a 15% solution of methanol/water (80:20). 159 mg of Baccatin III were recovered resulting in a 66% yield. The $^1$H NMR analysis and melting point of the product matched values previously reported in the literature for Baccatin III.

TABLE VIb

| | |
|---|---|
| Reaction Solvent | glyme |
| with | NaBH$_4$ |
| Reaction temp C. | room temperature |
| Reaction time | 72 hours |
| Theoretical yield Baccatin III | 241 mg |
| Actual yield Baccatin III (hplc) | 159 mg |
| % yield Baccatin III | 66% |
| Taxol remaining (hplc) | 19 mg |
| % taxol remaining | 5% |
| Cephalomannine remaining | 33 mg |
| % cephalomannine remaining | 14% |

The same reaction as described in Example VI above was performed using diglyme, a higher molecular weight solvent, and a 52% yield resulted. In contrast, the same reaction was run for one hundred forty-four hours using no tin chloride and triglyme. Here, the yield was 46%. Again, in contrast, the baseline Magris, et al procedure which is run at 0° C. and is economically not as attractive resulted in a 66% yield when the mixture was 47% taxol. The yield in Example VI is from starting material that is only 3.5% taxol. As noted when the reaction was run for one hundred twenty hours at room temperature using dichloromethane as the reaction solvent, the result was only 53% Baccatin III. The use of apolar donor solvents like glyme and THF in the presence of a Lewis acid appears to result in substantially better yields of Baccatin III from partially purified taxanes starting material (with less than 50% taxol) than the use of CH$_2$Cl$_2$ (an apolar, nondonor solvent) in the presence of a Lewis acid.

EXAMPLE VII

The reaction conditions and starting material in Example VII are as follows:

TABLE VIIa

| | |
|---|---|
| Starting material (mass) | 10 g |
| Taxol in starting material | 350 mg |
| % taxol in starting material | 3.5% |
| Ceph in starting material | 230 mg |
| % Ceph in starting material | 2.3% |
| Reducing salt | NaBH$_4$ (pellets) 10:1 |
| Additional reagents | CoCl$_2$ (7%) |

10 g of taxane starting material containing a taxol (3.5%) and cephalomannine (2.3%) was stirred into 200 mL of glyme in a 500 mL round bottom flask under a nitrogen gas atmosphere. Sodium borohydride (10:1 stoichiometric ratio based on starting material) and 7% cobalt chloride (based on the molar percent of taxol in the starting material) were added to the reaction, in pellet form. The reaction was allowed to run at room temperature for one hundred forty-four hours. After the one hundred forty-four hour period, the organic solution containing the Baccatin III was then purified by the following method. The reaction mixture was poured into 10 m per gram of 50% by volume acetic acid/H$_2$O. The organic solution was then repeatedly extracted with an immiscible organic solvent, in this case glyme. The organic phase was collected and dried over anhydrous sodium sulfate. The organic phase was then evaporated under vacuum to a viscous oil. The oil was purified by flash chromotography eluting with dichloromethane/5% methanol. The selected fractions were then evaporated to dryness under reduced pressure (20 mm Hg). The dry organic material was then recrystallized in a 15% solution of methanol/water (80:20). 174 mg of Baccatin III were recovered resulting in a 72% yield. The proton NMR and melting point of the product matched the previously reported literature values for Baccatin III.

TABLE VIIb

| | |
|---|---|
| Reaction Solvent | glyme |
| with | NaBH$_4$/CoCl$_2$ pellets |
| Reaction temp C. | room temperature |
| Reaction time | 144 hours |
| Theoretical yield Baccatin III | 241 mg |
| Actual yield Baccatin III (hplc) | 174 mg |
| % yield Baccatin III | 72% |
| Taxol remaining (hplc) | 25 mg |
| % taxol remaining | 7% |
| Cephalomannine remaining | 45 mg |
| % cephalomannine remaining | 20% |

EXAMPLE VIII

Ethanol was selected as a solvent even though Magris, et al reported sodium borohydride and isopropyl alcohol resulted in an undesirable mixture of Baccatin III, Baccatin V and diol 8. A surprising result developed when the procedure as shown below was performed without a Lewis acid and ethanol as the reaction solvent. The result was that at −30° C. the sodium borohydride in a 10:1 stoichiometric quantity selectively cleaved cephalomannine and other taxanes over taxol. The reaction conditions and starting material in Example VIII are as follows:

TABLE VIIIa

| Starting material (mass) | 10 g |
|---|---|
| Taxol in starting material | 350 mg |
| % taxol in starting material | 3.5% |
| Ceph in starting material | 230 mg |
| % Ceph in starting material | 2.3% |
| Reaction Solvent | ethanol |
| with | NaBH₄ |
| Reaction temp C. | −30° C. |
| Reaction time | 24 hours |
| Reducing salt | NaBH₄ 10:1 |
| Additional reagents | none |

10 grams of taxane starting material containing 3.5% taxol and 2.3% cephalomannine was stirred into 200 ml of ethanol in a 500 ml round bottom flask under a nitrogen gas atmosphere. The solution was cooled to −30° C. and a 10:1 stoichiometric quantity of sodium borohydride was added to the mixture. The reaction was allowed to stir for twenty-four hours. The mixture was then poured into a 10–25 ml per gram solution of 50% by volume acetic acid/H$_2$O. The organic solution was repeatedly extracted with an immiscible organic solvent, in this case dichloromethane. The organic phase was collected, dried over anhydrous sodium sulfate, and reduced in vacuo to a viscous oil. The oil was purified by flash chromotography eluting with dichloromethane/5% methanol. The selected fractions were evaporated to dryness under reduced pressure (20 mm Hg). The organic material was recrystallized from a 15% solution of methanol/H$_2$O in an 80:20 ratio. A 58% yield of Baccatin III was realized according to HPLC analysis. The HPLC analysis also indicated there was 100% of the taxol remaining. The yield of Baccatin III therefore came from cephalomannine and other non-taxol taxanes. The $^1$H NMR and melting point of the final product matched those previously reported for Baccatin III.

TABLE VIIIb

| Theoretical yield Baccatin III | 241 mg |
|---|---|
| Actual yield Baccatin III (hplc) | 140 mg |
| % yield Baccatin III | 58% |
| Taxol remaining (hplc) | 350 mg |
| % taxol remaining | 100% |
| Cephalomannine remaining | 193 mg |
| % cephalomannine remaining | 84% |

To determine without undue experimentation which Lewis acids will produce high yields of Baccatin III from a mixture of partially purified taxanes, the following two step test must be analyzed. First, the Lewis acid should be able to covalently bond with strong nucleophilic species including, for example, oxygen anions. Thus, magnesium chloride will not be a preferred Lewis acid. Second, the Lewis acid must not react with the borohydride reducing salt to form boranes (B$_2$H$_6$). Lewis acids that can covalently bond with strong nucleophiles and do not react to form boranes can be used in the present invention. For example, Lewis acids such as SbCl$_5$, ZnCl$_2$, CuCl$_2$, PbCl$_2$, GeCl$_2$, SnBr$_2$, SnI$_2$ and CoBr$_2$ would be selected Lewis acids under the two step test.

Various experiments indicate that large scale production of Baccatin III may require more than 0.1% of the Lewis acid. Furthermore, when large quantities of starting material are used it is extremely important to closely monitor the reaction by TLC and to be certain that the mixture is being well agitated so that the cleavage reaction can readily occurs.

The present invention discloses new high yield processes for converting partially purified taxane mixtures into Baccatin III. These processes result in high yield of essentially pure Baccatin III after purification. Characterization of the resultant species confirms the structure of the resultant product to be Baccatin III. In addition to the high yield of Baccatin III these processes are commercially viable, inexpensive, and run at room temperature. In addition, the process when run with an alcohol solvent at −30° C. cleaves cephalomannine and other taxanes selectively without converting the taxol. The use of the borohydride reducing salts other than sodium borohydride and tetrabutylammonium borohydride and the use of other Lewis acids are contemplated by this invention.

Accordingly, the present invention has been described with some degree of particularity directed to the processes of the present invention. It should be appreciated, though, that the present invention is defined by the following claims construed in light of the prior art so that modifications or changes may be made to the processes of the present invention without departing from the inventive concepts contained herein. It is understood that the invention may be practiced otherwise than as specifically described.

I claim:

1. A process for the preparation of a compound of formula (I)

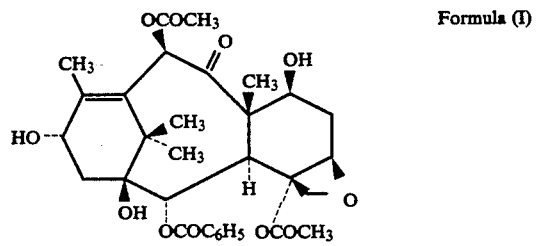

Formula (I)

comprising contacting a mixture containing at least one taxane compound having an ester linkage at the C-13 position with at least one borohydride reducing salt in a reaction solvent in the presence of a Lewis acid.

2. The process of claim 1 conducted at a range temperature of from room temperature to −30° C.

3. The process of claim 1 wherein the borohydride reducing salt is sodium borohydride.

4. The process of claim 1 wherein the borohydride reducing salt is tetrabutylammonium borohydride.

5. The process of claim 1 wherein the reaction solvent is selected from the group consisting of: CH$_3$OCH$_2$CH$_2$OCH$_2$, CH$_3$OCH$_2$CH$_2$OCH$_2$CH$_2$OCH$_3$, and CH$_3$OCH$_2$CH$_2$OCH$_2$CH$_2$OCH$_2$CH$_2$OCH$_3$.

6. The process of claim 1 wherein the reaction solvent is tetrahydrofuran.

7. The process of claim 1 wherein the reaction solvent is dichloromethane.

8. The process of claim 1 wherein the mixture contains at least 15%–50% taxanes which are taxol and the reaction solvent is tetrahydrofuran.

9. The process of claim wherein the mixture contains greater than 50% by weight of taxanes which are taxol and the reaction solvent is dichloromethane.

10. The process of claim 1 wherein the mixture contains less than 15% by weight of taxanes which are taxol and the reaction solvent is selected from the group consisting of $CH_3OCH_2CH_2OCH_3$, $CH_3O(CH_2CH_2O)CH_3$, and $CH_3O(CH_2CH_2O)_3CH_3$.

11. The process of claim 1 wherein the Lewis acid is a metal halide.

12. The process of claim 11 wherein the metal halide is tin chloride.

13. The process of claim 11 wherein the metal halide is cobalt chloride.

14. A process for the preparation of a compound of formula (I)

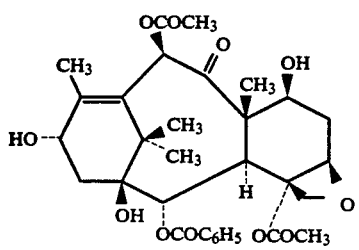

Formula (I)

comprising contacting a mixture containing at least one taxane compound constituent having an ester linkage at the C-13 position with a borohydride reducing salt in aromatic hydrocarbons.

15. The process according to claim 14 wherein said aromatic hydrocarbon is toluene 16. The process according to claim 14 wherein said borohydride reducing salt is tetrabutylammonium borohydride.

17. The process according to claim 14 is conducted at a temperature of 0° C.

18. A process for the preparation of a compound of formula (I)

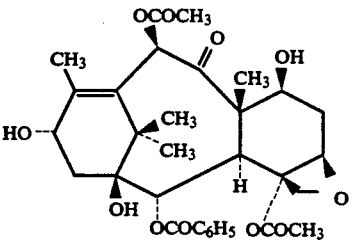

Formula (I)

comprising contacting a mixture containing a taxane compound which is taxol and at least one other taxane compound having an ester linkage at the C-13 position that is not taxol with a borohydride reducing salt in a reaction solvent wherein the taxane compound which is taxol in the mixture is not converted to formula I as defined above.

19. The process according to claim 18 wherein the reducing salt is sodium borohydride.

20. The process according to claim 19 wherein the reaction solvent is ethanol.

21. The process according to claim 20 conducted at a temperature of −30° C.

* * * * *